United States Patent [19]
Dolan

[11] Patent Number: 5,582,194
[45] Date of Patent: Dec. 10, 1996

[54] SINGLE USE DENTAL FLOSS DISPENSER

[75] Inventor: John W. Dolan, Boothwyn, Pa.

[73] Assignee: W. L. Gore & Associates, Inc., Newark, Del.

[21] Appl. No.: 527,985

[22] Filed: Sep. 14, 1995

[51] Int. Cl.$^6$ ................................................. A61C 15/00
[52] U.S. Cl. ............................................ 132/321; 206/63.5
[58] Field of Search ................................... 132/321, 323, 132/324; 433/143; 206/380, 104, 134, 38, 63.5, 368

[56] References Cited

U.S. PATENT DOCUMENTS

| | | |
|---|---|---|
| D. 339,426 | 9/1993 | Spencer, Jr. . |
| 3,094,209 | 6/1963 | Krupp . |
| 4,712,572 | 12/1987 | Hovel, III . |
| 4,807,752 | 2/1989 | Chodorow . |
| 4,852,728 | 8/1989 | Court . |
| 4,972,946 | 11/1990 | Whittaker . |
| 4,986,289 | 1/1991 | McWhorter . |
| 5,024,324 | 6/1991 | Whittaker . |
| 5,156,311 | 10/1992 | Spencer, Jr. et al. . |
| 5,249,674 | 10/1993 | Lepie . |

Primary Examiner—Todd E. Manahan
Attorney, Agent, or Firm—Victor M. Genco, Jr.

[57] ABSTRACT

In one aspect of the present invention a single use dental floss dispenser comprises a tri-fold assembly having a base portion and first and second covering portions. The first and second covering portions are foldably attached to the base portion along respective first and second folds. The first and second covering portions are foldable onto the base portion to define an enclosure having an interior. A predetermined length of dental floss is contained within the interior of the enclosure. The length of dental floss has opposed first and second ends. At least the first end of the length of dental floss is attached to an interior surface of the first covering portion. An unfolding motion of the first covering portion from a folded position, wherein the first covering portion is folded onto the base portion, to an unfolded position, draws a predetermined grippable portion of the length of dental floss from the enclosure interior to facilitate the complete removal of the length of dental floss from the enclosure interior.

7 Claims, 3 Drawing Sheets

SINGLE USE DENTAL FLOSS DISPENSER

FIELD OF THE INVENTION

This invention generally relates to oral hygiene, and particularly to an improved single use dental floss dispenser for facilitating oral prophylaxis.

BACKGROUND OF THE INVENTION

It is well understood that dental floss use is an important part of a total oral hygiene program. Although toothbrush use helps reduce plaque on the occlusal surfaces of the teeth, floss use reduces plaque accumulation in the interstitial surfaces of the teeth. Caries will develop on surfaces where there is an accumulation of plaque. Dental floss is an effective means to disrupt the accumulation of plaque in the interstitial regions of the teeth, thereby reducing the likelihood for the development of caries on tooth surfaces. Accordingly, flossing helps prevent periodontal diseases, such as gingivitis.

Dental floss has commonly been manufactured and distributed as a spool of thread-like material which is housed in a plastic dispensing container. The user withdraws a length of floss from the container and then severs the length from the spool. The user then wraps the floss about his or her fingers for manipulation and insertion of the floss between the teeth. Alternately, a length of floss may be mounted on a flossing instrument. An individual who employs flossing as a hygienic dental practice, commonly carries a container housing such as a spool of dental floss. A suitable plastic dental floss dispensing container which has been employed in the past is disclosed in U.S. Pat. No. 5,156,311 and U.S. Pat. No. Des. 339,426. Even though such a container is relatively compact, it nonetheless may present undesirable bulk in a person's pockets.

As may be appreciated from the foregoing, there is a need for a single use dental floss dispenser for dispensing a usable quantity of dental floss in such a manner that the dispenser maintains the dental floss in a sanitary condition prior to use. Such a dispenser should be dimensioned to be readily carried in a pocket, billfold or otherwise. As such, the single use dental floss dispenser would function as a personal unit to suit the oral hygiene requirements of a traveling person. Such a single use dental floss dispenser also may be effectively employed in a medical and/or dental environment. In such a use, a medical or dental patient is assured that the sanitary integrity of the floss employed by medical and/or dental personnel has not been comprised.

To date, numerous methods and devices have been employed to distribute advertising materials to consumers. Conventional mass advertising methods have included inserting printed advertising literature into books, magazines, newspapers, or the like. Also, advertising pouch assemblies have been employed to distribute advertising literature via the postal system. However, as competition for consumer spending has escalated, actual product distribution has been employed as a preferred form of advertising in many instances. In the past, product distribution for advertising purposes has been carried out by supplying to consumers complimentary product samples, such as by bulk mailing such product samples to a targeted consumer sector, for example. Also, product samples in the form of swatches, food samples, perfumes, soaps, records, and films previously have been distributed within magazines. These type of product samples have made taste, touch, smell, sound and sight a reality in magazine advertising.

There is a need for an improved single use dental floss dispenser which may also serve as an advertising premium to be treasured by a recipient thereof. Such an improved single use dental floss dispenser should not only function as a floss containment vessel, but should facilitate the dispensing of the contained floss in a fashion that does not require the destruction of the dispenser. Accordingly, even after the dental floss has been removed from the dispenser, the dispenser may still function as an advertising premium.

SUMMARY OF THE INVENTION

In one aspect of the present invention a single use dental floss dispenser comprises a tri-fold assembly having a base portion and first and second covering portions. The first and second covering portions are foldably attached to the base portion along respective first and second folds. The first and second covering portions are foldable onto the base portion to define an enclosure having an interior. A predetermined length of dental floss is contained within the interior of the enclosure. The length of dental floss has opposed first and second ends. At least the first end of the length of dental floss is attached to an interior surface of the first covering portion. A sealing means is provided for sealing predetermined perimetral edge surfaces of the first and second covering portions to the base portion. An unfolding motion of the first covering portion from a folded position, wherein the first covering portion is folded onto the base portion, to an unfolded position, draws a predetermined grippable portion of the length of dental floss from the enclosure interior to facilitate the complete removal of the length of dental floss from the enclosure interior.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings.

DETAILED DESCRIPTION OF THE INVENTION

Figure 1:
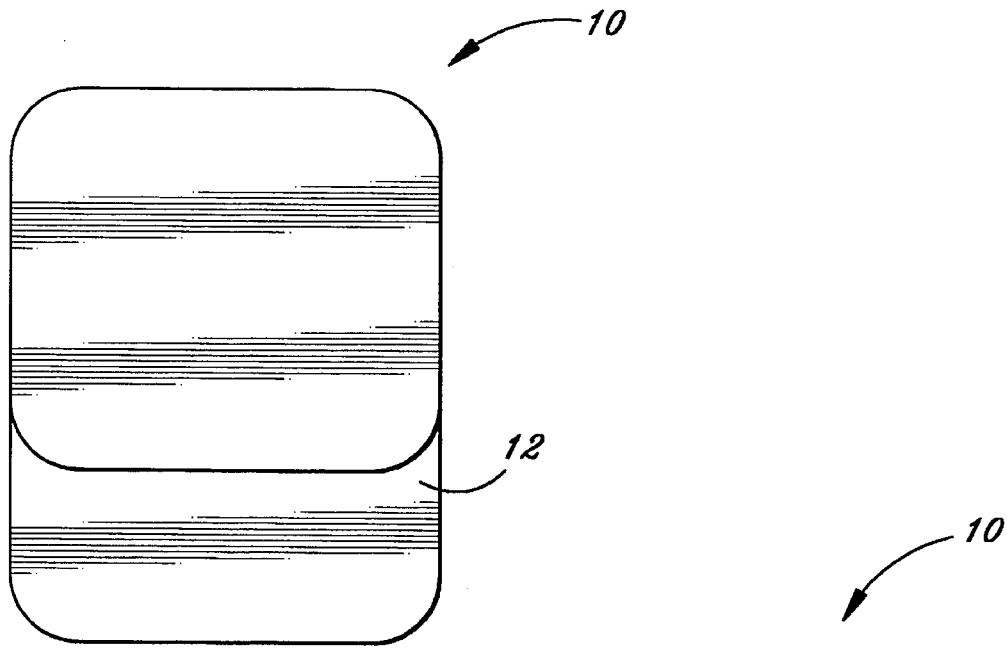
FIG. 1 is a front elevational view of the single use dental floss dispenser of the present invention; shown in a closed or sealed disposition.
Figure 2:
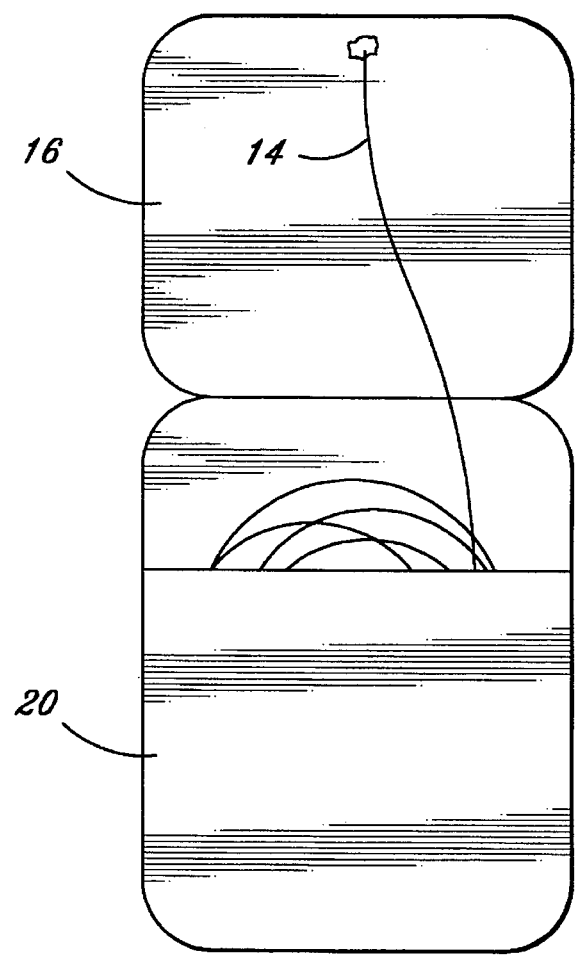
FIG. 2 is a front elevational view of the single use dental floss dispenser of FIG. 1, shown in an open or dispensing disposition.

Referring now to the drawings, wherein similar reference characters designate corresponding parts throughout the several views, the single use dental floss dispenser of the present invention is generally illustrated at 10 in FIGS. 1 and 2. The single use dental floss dispenser includes a container or envelope 12 and a predetermined length of dental floss 14.

As the term "dental floss" is used herein, it is intended to mean a thread-like material suitable for facilitating oral prophylaxis.

As best seen by a comparison of FIGS. 1–4, the container or envelope 12 is substantially planar in design, having a tri-fold construction. More particularly, the envelope 12 comprises a lid portion 16, a base portion 18, and a cover portion 20. The lid portion 16 is integrated with the base portion 18 along a fold 22. The cover portion 20 is integrated with the base portion 18 along a fold 24. Folds 22 and 24 are substantially parallel with respect to each other, and folds 22 and 24 are arranged generally perpendicular to lateral edge surfaces 25 of the envelope 12.

The length of both the lid portion 16 and the cover portion 20 is approximately sixty-nine percent the length of the base portion 18. As best seen by comparing FIGS. 1–4, to form the envelope 12, the cover portion 20 is first folded along fold 24 onto the base portion 18 to partially cover the dental floss 14. Thereafter, the lid portion 16 is folded along fold 22 onto the remaining uncovered base portion 18, and onto and overlapping the folded cover portion 20. The length-to-width ratio of the closed single use dental floss dispenser 10 of FIG. 1 is about 1.25:1.

The perimeter of the width portion of the envelope 12 is sealed so as to create an internal cavity for containing a single length of dental floss 14. The dental floss 14 may be arranged in the cavity in a coil, or may be disposed within the cavity in no preset arrangement, such as may be accomplished when the dental floss is blown into the envelope with air, for example. The choatic arrangement of the floss length within the envelope provides for a less build-up of planar thickness to the sachet envelope thus reducing the overall height of a stacked pile of sachet units. The reduced height of the stack pile minimizes the overall size of packaging boxes. Also, if used in a magazine, provides for less bulk as compared to a wound coil of a floss length. The perimeter of the envelope 12 may be sealed by any suitable means 26, such as by glues, or hot or cold melt adhesives which are approved by the Food and Drug Administration (FDA) for class 1 medical devices.

The envelope 12 may be comprised of a paper material, a plastic material, or any other suitable material which is at least partially impermeable to water. If a paper material is employed, the paper material may be coated with a suitable material to make it less permeable to water. Although materials such as cellophane, or synthetic fiber sheets, such as a TYVEK® brand synthetic fiber sheets from E. I. dupont de Nemours and Company, may be employed for use as the envelope 12, hot and cold melt adhesives tend to provide a more effective adherence to paper and fibrous materials. (TYVEK is a registered trademark of E. I. dupont de Nemours and Company.) Also, as is well known, hot and cold melt adhesives typically have a longer shelf life as compared to pressure sensitive adhesives, which are effective in bonding plastic materials.

Figure 3:
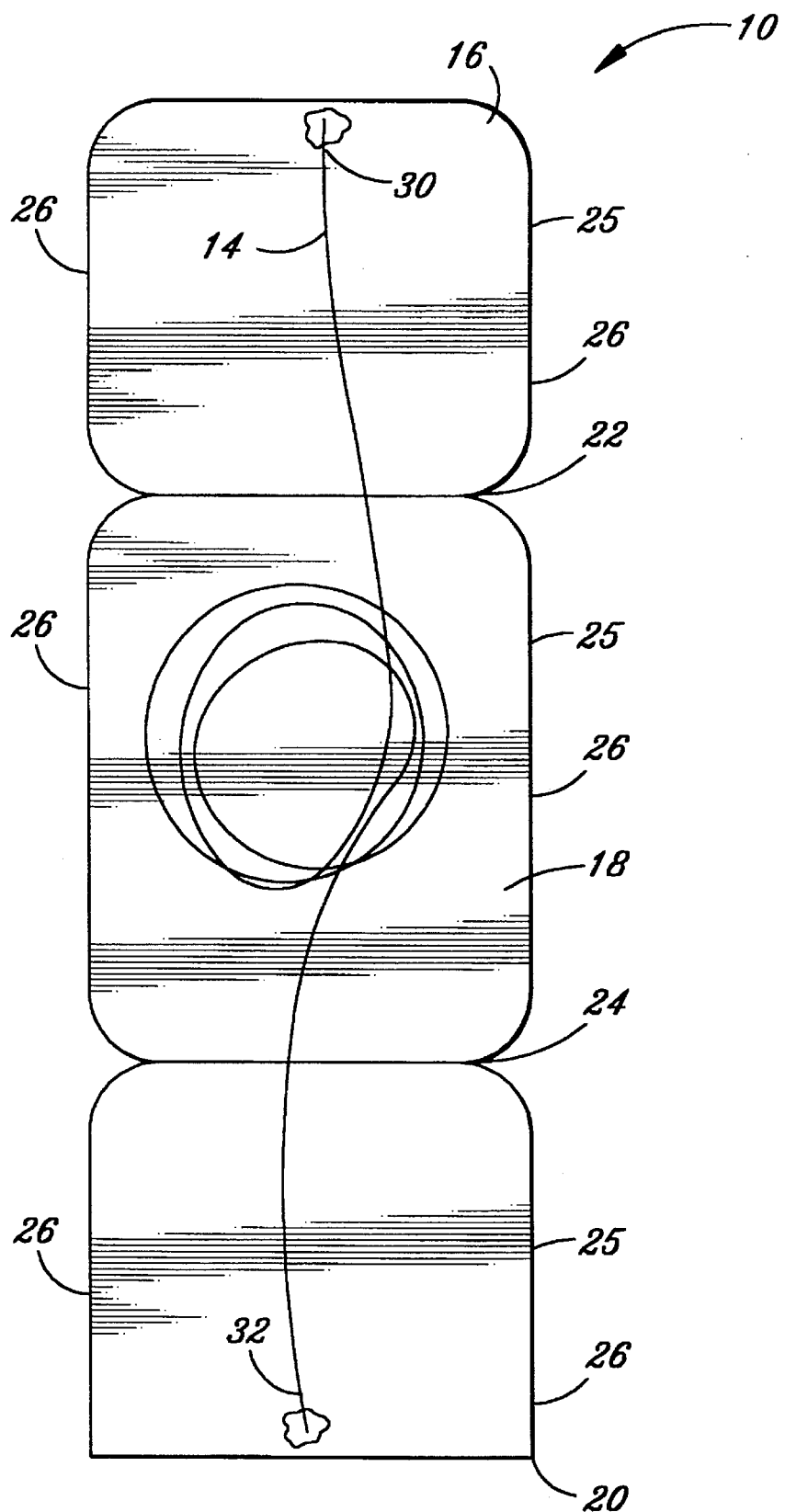
FIG. 3 is a top plan view of the single use dental floss dispenser of FIG. 1, shown in an unfolded, pre-assembled disposition.
Figure 4:
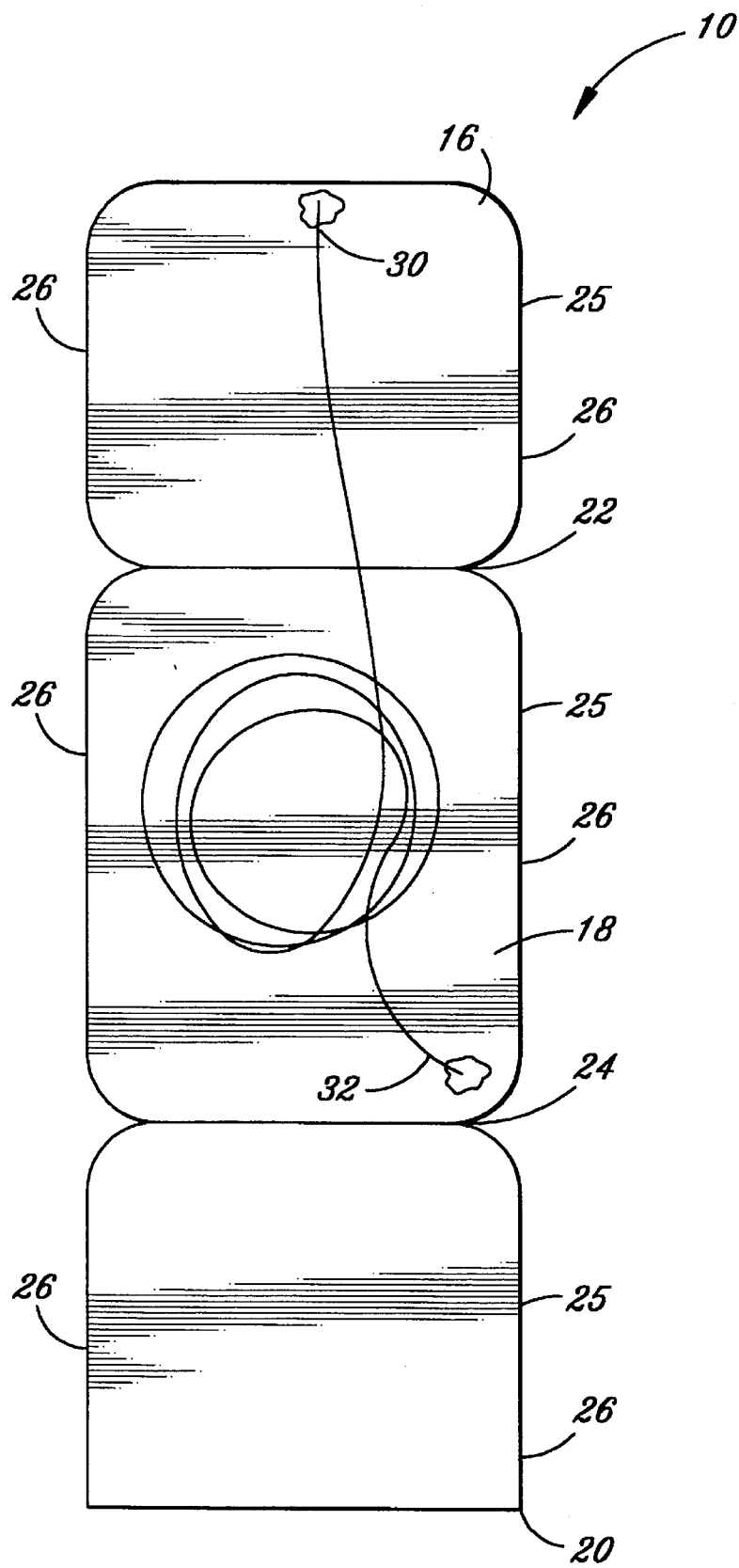
FIG. 4 is a top plan view of an alternate embodiment of the single use dental floss dispenser of the present invention, shown in an unfolded, preassembled disposition.

As best seen by reference to FIG. 3, the length of dental floss 14 has a first end 30 and a second end 32. In the embodiment illustrated in FIG. 3, the first end 30 is attached to the interior surface of the lid portion 16, and the second end 32 is attached to the interior surface of the cover portion 20. FIG. 4 is similar to FIG. 3, except that the second end 32 is attached to the interior surface of the base portion 18.

As should be understood, at least the first end 30 is attached to the interior surface of the lid portion 16 to permit the dispenser 10 to operate in accordance with the teachings herein. The second end 32 may be attached to the interior surface of the lid portion 16, the base portion 18 or the cover portion 20. Ends 30 and 32 may be attached to the envelope 12 by any suitable means, such as by a suitable adhesive, for example. If an adhesive is employed for such a purpose, the adhesive should be of a type approved by the FDA for class 1 medical devices.

The single use dental floss dispenser not only functions as a dental floss containment vessel, but also facilitates the dispensing of the length of dental floss from within the interior of the envelope 12. More particularly, as best seen by reference to FIGS. 1 and 2, the length of dental floss is presented to a user thereof as the lid portion 16 is opened (FIG. 2). In this regard, as the lid portion 16 is opened, the dental floss 14, being secured to the interior surface of the lid portion 16, creates an arch along the length of the floss starting from the underside of the lid portion 16 and down to the top of the cover portion 20. Accordingly, a user may easily grab the arched dental floss 14 from the envelope 12 and pull out the entire length of dental floss from the envelope.

The length of dental floss 14 may be comprised of any suitable material which may be useful in reducing plaque accumulation in the interstitial surfaces of the teeth. For purposes of example only, and without intending to limit the scope of the present invention in any manner, the dental floss 14 may comprise, in part, a polytetrafluoroethylene (PTFE) fiber material that is essentially rectangular to oblong in cross-sectional dimensions. The fiber may be formed with or without folds. In a folded embodiment, prior to folding, the PTFE fiber has typical dimensions of about 40 $\mu$m in thickness and about 2 mm in width. When this material is folded and packaged as dental floss, the material typically has dimensions of about 90 $\mu$m in thickness and about 1.2 mm in width in an unfolded embodiment of the present invention, the PTFE fiber material forms essentially a rectangular to oblong cross-sectional dimension having typical dimensions of about 50 to 250 $\mu$m, and preferably 75 to 150 $\mu$m, in thickness, and about 0.5 to 3 mm, and preferably 0.7 to 1.5 mm, in width. The substantial thickness of this material allows the floss to function extremely well without need for folding or otherwise bulking the height of the material.

The PTFE fiber material may be formed as taught in U.S. Pat. No. 3,543,566 to Gore, incorporated by reference. The preferred sheet comprises a thickness of about 0.5 to 1.0 mm; a density of about 0.8 to 1.5 g/cc; and a tenacity of about 0.5 to 1.0 g/tex.

Each of these properties are measured in a conventional manner. Width and thickness is determined through any conventional means, such as through the use of calipers or through measurements through a scanning electron microscope. Density is determined by dividing the measured weight of the sample by the computed volume of the sample. The volume is computed by multiplying the measured length, width, and thickness of the sample. Tenacity is calculated by dividing the sample's tensile strength by its normalized weight per unit length (tex [grams/1000 meters] or denier [grams/9000 meters]).

This sheet may then be slit into strands by passing the sheets through a series of gapped blades set 0.5 to 20 mm apart. Finally, the fibers should be wound onto a spool with care taken to avoid rolling or folding of the fibers during the spooling process.

Preferably, an expanded PTFE sheet is formed and slit into fibers in the following manner. A fine powder PTFE resin is blended with a lubricant, such as odorless mineral spirits, until a compound is formed. The volume of lubricant used should be sufficient to lubricate the primary particles of the PTFE resin so to minimize the potential of the shearing of the particles prior to extruding.

The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications a reduction ratio of 75:1 to 100:1 is preferred.

The lubricant may then be removed, such as through volatilization, and the dry coherent extrudate is expanded in at least one direction about 1.1 to 50 times its original length (with about 1.5 to 2.5 times being preferred). Expansion may be accomplished by passing the dry coherent extrudate over a series of rotating heated rollers or heated plates.

Once this sheet is formed, the sheet may be formed into a fiber by slitting the dry coherent expanded extrudate into predetermined widths by passing it between a set of gapped blades or other cutting means. Following cutting, the slit coherent extrudate may then be further expanded in the longitudinal direction at a ratio of 1:1.1 to 50:1 (with 15:1 to 35:1 being preferred) to form a fiber. Finally, this fiber may be subjected to an amorphous locking step by exposing the fiber to a temperature in excess of 342° C.

The width of the fiber can be controlled by several process variables known in the art of expanded PTFE. Variables which can affect the width of the fiber are: slit width, expansion temperatures and expansion ratio.

The final dimensions of a suitable PTFE fiber material may comprise: a width of about 0.5 to 3.0 mm; a thickness of about 50 to 250 ∞m; a weight/length of about 80 to 450 tex; a density of about 1.0 to 1.9 g/cc; a tensile strength of about 1.5 to 15 kg; and a tenacity of about 10 to 40 g/tex.

Again, these measurements were made in a conventional manner. Bulk tensile strength was measured by a tensile tester, such as an INSTRON Machine of Canton, Mass. In the case of sheets goods, the INSTRON machine was outfitted with clamping jaws which are suitable for securing the sheet goods during the measurement of tensile loading. The cross-head speed of the tensile tester was 25.4 cm per minute. The gauge length was 25.4 cm. In the case of fibers, the INSTRON machine was outfitted with fiber (horn type) jaws that are suitable for securing fibers and strand goods during the measurement of tensile loading.

Although a few exemplary embodiments of the present invention have been described in detail above, those skilled it the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. A single use dental floss dispenser comprising:

a tri-fold assembly having a base potion and first and second covering portions, the first and second covering portions being foldably attached to the base portion along respective first and second folds, said first and second covering portions being foldable onto the base portion to define an enclosure having an interior;

a predetermined length of dental floss having opposed first and second ends, wherein at least the first end of the length of dental floss is attached to an interior surface of the first covering portion, the length of dental floss being contained within the interior of the enclosure; and means for sealing predetermined perimetral edge surfaces of the first and second covering portions to the base portion;

wherein an unfolding motion of the first covering portion from a folded position, wherein the first covering portion is folded onto the base portion, to an unfolded position, draws a predetermined grippable portion of the length of dental floss from the enclosure interior to thereby facilitate the complete removal of the length of dental floss from the enclosure interior.

2. The single use dental floss dispenser of claim 1, wherein a length to width ratio of the single use dental floss dispenser in a folded and sealed disposition is about 1.25:1.

3. The single use dental floss dispenser of claim 1, wherein the first and second covering portions each have a length dimension which is about 69% of a length dimension of the base portion.

4. The single use dental floss dispenser of claim 1 or 3, wherein the first and second covering portions are folded onto the base portion in an overlapping relation such that the first covering portion overlaps on top of the second covering portion.

5. The single use dental floss dispenser of claim 1, wherein the sealing means is a hot melt adhesive.

6. The single use dental floss dispenser of claim 1, wherein the sealing means is a cold melt adhesive.

7. The single use dental floss dispenser of claim 1, wherein the length of dental floss is at least in part comprised of polytetrafluoroethylene.

* * * * *